United States Patent
Ahmad et al.

(10) Patent No.: US 7,270,965 B2
(45) Date of Patent: Sep. 18, 2007

(54) ASSAYS TO SCREEN FOR COMPOUNDS THAT BIND THE DORSAL ROOT RECEPTOR

(75) Inventors: Sultan Ahmad, St Laurent (CA); Eric Grazzini, St Laurent (CA); Thierry Groblewski, St Laurent (CA); Paolo Lembo, St Laurent (CA); Ralf Schmidt, St Laurent (CA)

(73) Assignee: AstraZeneca AB, Sodertalje (SE)

( * ) Notice: Subject to any disclaimer, the term of this patent is extended or adjusted under 35 U.S.C. 154(b) by 376 days.

(21) Appl. No.: 10/399,181

(22) PCT Filed: Oct. 16, 2001

(86) PCT No.: PCT/SE01/02264

§ 371 (c)(1),
(2), (4) Date: Apr. 14, 2003

(87) PCT Pub. No.: WO02/33416

PCT Pub. Date: Apr. 25, 2002

(65) Prior Publication Data

US 2005/0059575 A1    Mar. 17, 2005

Related U.S. Application Data

(60) Provisional application No. 60/240,889, filed on Oct. 17, 2000.

(51) Int. Cl.
*G01N 33/53* (2006.01)
*G01N 33/534* (2006.01)
*G01N 33/535* (2006.01)
*C12Q 1/68* (2006.01)

(52) U.S. Cl. .................. 435/7.2; 435/7.92; 435/7.93; 435/6

(58) Field of Classification Search .................. None
See application file for complete search history.

(56) References Cited

U.S. PATENT DOCUMENTS 4,388,236 A   6/1983   Stein
5,367,053 A   11/1994  Dooley et al.

FOREIGN PATENT DOCUMENTS

EP    1118621      7/2001
WO    WO9932519    7/1999
WO    WO 0183555   11/2001

OTHER PUBLICATIONS

Thomas Walther et al. "Sustained Long Term Potentiation and Anxiety in Mice Lacking the Mas Protooncogene," The Journal of Biological Chemistry, May 8, 1998, p. 11867-11873, vol. 273 (No. 19), The American Society for Biochemistry and Molecular Biology, Inc., U.S.A.

Paola Lembo et al., "Proenkephalin A Gene Products Activate a New Family of Sensory Neuron-Specific GPCRs", Nature Neuroscience, Mar. 2002, pp. 201-209, vol. 5, No. 3, Nature Publishing Group.

*Primary Examiner*—Ruixiang Li
(74) *Attorney, Agent, or Firm*—Robin S. Quartin

(57) ABSTRACT

The present invention is directed to assays that can be used to screen for compounds that act as agonists or antagonists or inverse agonists of bovine adrenal medulla docosapeptide (BAM-22P). The assays are based upon the binding of BAM-22P to the rat and human DRR receptors.

4 Claims, No Drawings

ASSAYS TO SCREEN FOR COMPOUNDS THAT BIND THE DORSAL ROOT RECEPTOR

CROSS-REFERENCE TO RELATED APPLICATIONS

This application is the National Stage of International Application No. PCT/SE01/02264, filed Oct. 16, 2001, which claims the benefit under 35 U.S.C. §119(e) of U.S. Provisional Application 60/240,889, filed Oct. 17, 2000.

FIELD OF THE INVENTION

The present invention is directed to assay methods that can be used to determine whether a test compound has activity as a modulator of the binding and activity of BAM-22P at the rat and human DRRs. Compounds identified as being effective modulators have potential use as therapeutic agents in treating pain, neuropathic and inflammatory disorders.

BACKGROUND OF THE INVENTION

A. Bovine Adrenal Medulla docosapeptide

BAM22 Peptide: YGGFMRRVGRPEWWMDYOKRYG-OH.

The preproenkephalin A (PPA) cDNA was cloned in 1983 (Nature 297:431-434, 1982). The PPA gene contains several basic amino acids within its coding sequence which can give rise to several peptides upon protease cleavage. Such peptide cleavage products include BAM12P, BAM20P, BAM22P, MEAGL, MEAP and Peptide E and F (Bovine adrenal medulla). Some of these peptides have been implicated in neuronal survival, and analgesia (Int. J. Devl. Neuroscience 10, No2.pp171-179, 1992, Eur. J. Pharmacol., 85,355-356, 1982).

BAM-22P is a peptide precursor of Met-enkephalins (Mizuno, *Biochem. Biophys. Res. Commun.* 97 (4): 1283-90 (1980). In mammals, BAM-22P has been shown to be present (by immunoreactivity) in peripheral tissue such as the adrenal medulla, islets of Langerhans (Timiners, *Diabetes.;* 35 (1):52-7 (1986)) and in the central nervous system including many hypothalamic and thalamic nuclei, inteipeduncular nucleus, substantia nigra, the colliculi, periaqueductal gray, parabrachial nuclei, trigeminal motor and spinal nuclei, nucleus raphe magnus and other raphe nuclei, nucleus reticularis paragigantocellularis, vestibular nuclei, several noradrenergic cell groups, nucleus tractus solitarius, as well as in the dorsal horn of the spinal cord (Khachiaturian, *J. Comp. Neurol.* 220 (3):310-20 (1983).

Although the precise physiological activity of BAM-22P in mammals is not known, it has been implicated in motor coordination and analgesia (J. Pharmacol Exp Ther 1986 September; 238 (3):1029-1044, Eur. J. Pharmacol., 85.355-356, 1982).

BAM-22P is an orphan peptide and its specific receptor has not been identified despite its known ability to bind to the mu, delta and kappa opioid receptors. The present inventors have discovered that BAM-22P is able to activate mammalian dorsal root receptors (DRR), including the rat and human DRR receptors.

B. G Protein-coupled Receptors

G protein coupled receptors (GPCRs) constitute a family of proteins sharing a common structural organization characterized by an extracellular N-terminal end, seven hydrophobic alpha helices putatively constituting transmembrane domains and an intracellular C-terminal domain. GPCRs bind a wide variety of ligands that trigger intracellular signals through the activation of transducing G proteins (Caron, et al., *Rec. Prog. Horm. Res.* 48:277-290 (1993); Freedman, et al., *Rec. Prog. Horm. Res.* 51:319-353 (1996)).

More than 300 GPCRs have been cloned thus far and it is generally assumed that there exist well over 1,000 such receptors. Roughly 50-60% of all clinically relevant drugs act by modulating the functions of various GPCRs (Gudermann, et al., *J. Mol. Med.* 73:51-63 (1995)). Many of the clinically relevant receptors are located in the central nervous system.

Among the GPCRs that have been identified and cloned is a gene that encodes a protein known as DRR which is homologous to the receptors of the mas oncogene family. A rat counterpart of DRR was found to be homologous and based upon the location of cells expressing DRR mRNA, it has been proposed that the receptor plays a role in transmission of pain. However, the endogenous ligand for this family of receptors has not previously been identified (Cell: 45, 711-719 1986, JBC 273,11867-11873 1998, WO 99/32519).

SUMMARY OF THE INVENTION

The present invention provides assays capable of identifying potential therapeutic compounds which are agonists or antagonists of the DRR receptor. Recombinant cells expressing either rat or human DRR can be used in conjunction with BAM-22P in screening assays designed to identify agonists and antagonists. Thus, in its first aspect, the invention is directed to a method of assaying a test compound for its ability to bind to the DRR receptor. This is accomplished by incubating cells expressing the receptor gene with BAM-22P and test compound. The extent to which the binding of BAM-22P is displaced is then determined. Radioligand assays or enzyme-linked immunosorbent assays may be performed in which either BAM-22P or the test compound is detectably labeled. Although any cell expressing DRR may be used, a recombinant cell expressing a heterologous DRR gene from either the rat or human is preferred. The term "heterologous" as used herein refers to any DRR gene transfected into a cell, i.e., the term refers to any non-endogenous DRR.

The invention also encompasses methods of determining if a test compound is an agonist, antagonist, or inverse agonist of BAM-22P binding based upon a functional assay. One way to carry out such assays is to incubate a cell expressing DRR with the test compound and to then determine whether intracellular phospholipase C, adenyl cyclase activity or intracellular calcium concentrations are modulated. Results should typically be compared with those obtained when incubations are performed in a similar manner but in the absence of test compound. In general, functional assays of this type will be performed in conjunction with binding assays of the sort described above. The preferred cell for use in the assays is a recombinant cell that has been transformed with a heterologous DRR gene. Test compounds that act as agonists should produce an increase in phospholipase C, decrease or increase in adenylyl cyclase activity or increase in intracellular levels of calcium. Inverse agonists may reduce phospholipase C activity or intracellular calcium levels, particularly if assays are performed in the presence of a fixed amount of BAM-22P. Antagonists, should block the binding of BAM-22P to the receptor but not produce the opposite response in terms of phospholipase C activity or intracellular calcium that is the hallmark of an inverse agonist.

DETAILED DESCRIPTION OF THE INVENTION

The present invention is directed to assays that can be used to screen compounds for their ability to modulate the binding of BAM-22P to the rat and human DRR receptors. Any form of BAM-22P that has been reported may be used, but the preferred peptide is 22 amino acids in length and has the sequence: BAM22 peptide: YGGFMRRVGRPEWWM-DYOKRYG-OH. (SEQ ID NO:1). This peptide may be obtained commercially (Bachem) or can be synthesized using standard methodology well known in the art. The peptide may be detectably labeled with radioisotopes such as $^{125}$I or, alternatively, fluorescent or chemiluminescent labels can be incorporated. Also, the peptide can be joined to enzymes that are readily detectable such as horseradish peroxidase.

The DRR receptor may be cloned from rat and/or human cells using known processes such as that described in WO 99/32519. The Examples section provides a detailed description of a procedure that may be used in cloning DRR. Once obtained, the DRR sequence should be incorporated into an expression vector with a promoter active in mammalian cells (Sambrook, et al., *Molecular Cloning: A Laboratory Manual,* 2nd Ed., Cold Spring Harbor Press (1989)). Examples of promoters that may be used include that of the mouse metallothionein I gene (Hamer, et al., *J. Mol. Appl. Gen.* 1:273-288 (1982)); the immediate-early and TK promoter of herpes virus (Yao, et al., *J. Virol.* 69:6249-6258 (1995); McKnight, *Cell* 31:355-365 (1982)); the SV 40 early promoter (Benoist, et al., *Nature* 290:304-310 (1981)); and, the CMV promoter (Boshart, et al., *Cell* 41:521-530 (1985)). Vectors may also include enhancers and other regulatory elements.

Once expression vectors have been constructed, they can be introduced into a mammalian cell line by methods such as calcium phosphate precipitation, microinjection, electroporation, liposomal transfer, viral transfer or particle mediated gene transfer. Although other mammalian cells may be used, HEK-293 cells have been found to give successful results and a procedure for expressing DRR in these cells is described in the Examples section. Standard procedures for selecting cells and for assaying them for the expression of DRR (e.g., by Northern analysis) may be performed.

Once the BAM-22P peptide and cells expressing the rat and human DRR receptors have been obtained, assays may be performed to determine whether test compounds have any effect on binding. A wide variety of different types of assays can be performed using standard methods well known in the art. For example, in radioligand binding assays, cells expressing DRRs are incubated with BAM-22P and with a compound being tested for binding activity. The preferred source of DRR is recombinantly transformed HEK-293 cells. Other cells may also be used provided they do not express other proteins that strongly bind BAM-22P. This can easily be determined by performing binding assays on cells transformed with DRR and comparing the results obtained with those obtained using their non-transformed counterparts.

Assays may be performed using either intact cells or with membranes prepared from the cells (see e.g., Wang, et al., *Proc. Natl. Acad. Sci. U.S.A.* 90:10230-10234 (1993)). As suggested above, the membranes, or cells, are incubated with BAM-22P and with a preparation of the compound being tested. After binding is complete, receptor is separated from the solution containing ligand and test compound, e.g., by filtration, and the amount of binding that has occurred is determined. Preferably, the ligand used is detectably labeled with a radioisotope such as $^{125}$I. However, if desired, other types of labels can also be used. Among the most commonly used fluorescent labeling compounds are fluorescein, isothiocynate, rhodamine, phycoerythrin, phycocyanin, allophycocyanin o-phthaldehyde and fluorescamine. Useful chemiluminescent compounds include luminol, isoluminol, theromatic of acridinium ester, imidazole, acridinium salt, and oxalate ester.

Nonspecific binding may be determined by carrying out the binding reaction in the presence of a large excess of unlabeled ligand. For example, labeled BAM-22P may be incubated with receptor and test compound in the presence of a thousandfold excess of unlabeled BAM-92P. Nonspecific binding should be subtracted from total binding, i.e., binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with receptor when, in fact, binding is being inhibited by some other mechanism. For example, the compound being tested should be in a buffer which does not itself substantially inhibit the binding of BAM-22P and should, preferably, be tested at several different concentrations. Preparations of test compound should also be examined for proteolytic activity and it is desirable that antiproteases be included in assays. Finally, it is highly desirable that compounds identified as displacing the binding of BAM-22P be reexamined in a concentration range sufficient to perform a Scatchard analysis on the results. This type of analysis is well known in the art and can be used for determining the affinity of a test compound for receptor (see e.g., Ausubel, et al., *Current Protocols and Molecular Biology,* 11.2.1-11.2.19 (1993); *Laboratory Techniques in Biochemistry and Molecular Biology,* Work, et al., Ed. N.Y. (1978)). Computer programs may be used to help in the analysis of results (e.g., Munson, P., *Methods Enzymol.* 92:543-577 (1983)).

Depending upon their effect on the activity of the receptor, agents that inhibit the binding of BAM-22P to receptor may be either agonists or antagonists. Activation of receptor may be monitored using a number of different methods. For example, phiospholipase C assays may be performed by growing cells in wells of a microtiter plate and then incubating the wells in the presence or absence of test compound total inositol phosphates (IP) may then be extracted in resin columns, and resuspended in assay buffer. Assay of IP thus recovered can be carried out using any method for determining IP concentration. Typically, phospholipase C assays will be performed separately from binding assays, but it may also be possible to perform binding phospholipase C assays on a single preparation of cells.

Activation of receptor may also be determined based upon a measurement of intracellular calcium concentration. For example, transformed HEK-293 cells may be grown on glass cover slides to confluence. After rinsing, they may be incubated in the presence of an agent such as Fluo-3, Fluo-4 and FURA-2 AM (Molecular Probe F-1221). After rinsing and further incubation, calcium displacement may be measured using a photometer. Other types of assays for determining intracellular calcium concentrations are well known in the ail and may also be employed.

Assays that measure the intrinsic activity of the receptor, such as those based upon inositol phosphate measurement, may be used in order to determine the activity of inverse agonists. Unlike antagonists which block the activity of agonists but produce no activity on their own, inverse agonists produce a biological response diametrically opposed to the response produced by an agonist. For example, if an agonist promoted an increase in intracellular calcium, an inverse agonist would decrease intracellular calcium levels.

The radioligand and cell activation assays discussed above merely provide examples of the types of assays that can be used for determining whether a particular test compound alters the binding of BAM-22P to the human/rat DRR receptors and acts as an agonist or antagonist. There are many variations on these assays that are compatible with the present invention. Such assays may involve the use of labeled antibodies as a means for detecting BAM-22P that has bound to receptor or may take the form of the fluorescent imaging plate reader assays described in the Examples section herein.

EXAMPLES

I. Methods

Preparation of Clone Rat and Human DRRs:

See Description in Patent WO 99/32519

Expression

REK-293 cells were transfected with a mammalian expression construct coding for the rat and human DRRs (pcDNA 3.0 vector, Invitrogen) using the Superfect reagent (Qiagen). A stable receptor pool of DRR was developed by applying a selection marker (G418, 0.9 mg/ml) and the cells were maintained in this selection medium. The presence of mRNA specific for clone DRR was assessed by Northern blot analysis and by the reverse transcriptase polymerase chain reaction (RT-PCR).

Ligands

In order to identify the ligand of clone rat and human DRRs, a collection of peptide and non-peptide ligands was obtained from commercial sources (Sigma, CalBiochem, American Peptide Company, Bachem, RBI, Phoenix). The compounds were dissolved in water/DMSO at 3 µM and placed in 96 well microplates. A total of 1000 compounds (peptides and non-peptides) were prepared and tested.

Assay

A functional assay was performed with FLIPR (Fluorescent Imaging Plate Reader, Molecular Devices) using the fluorescent calcium indicator Fluo-3 (Molecular Probes) on a 96 well platform. BEK-293 cells, either expressing the receptor or wild type cells, were loaded with Fluo-3 as follows. Stable HEK-293 clones expressing rat and human DRR or parental cells were plated at a density of 10,000 cells/well in a 96 well plate. On the day of the experiment, the DRR cells were loaded with fluorescent solution (Dulbecco's modified medium with 10% fetal bovine serum containing 4 µM Fluo-3 and 20% pluronic acid). The cells were incubated at 37 C for one hour in a humidified chamber. Following the incubation step, cells were washed five times in Hanks' with 20 mM Hepes and 0.1% BSA (pH 7.4). The cells were analyzed using the FLIPR system to measure the mobilization of intracellular calcium in response to different compounds.

II. Results

HEK-293 cells endogenously express some GPCRs such as bradykinin and PACAP receptors which can be used as internal controls for assays. The background signal was established with all of the compounds in the parental HEK-293 cells (non-transfected) using the FLIPR assay. HEK-293 cells expressing the clone DRR were stimulated with all compounds and calcium responses were compared with those in parental BEK-293 cells. Only one compound, bovine adrenal medulla docosapeptide (BAM-22P), consistently elicited signals in the transformed cells but not the wild type cells. This indicates that BAM-22P is interacting with the recombinantly expressed receptors. Confirmation of this conclusion was obtained by the observation of a dose-response relationship with BAM-22P in the cells transfected with DRR, but not in the non-transfected cells or in cells transfected with other orphan receptors. Thus, it has been established that clone rat and human DRR is a specific receptor for BAM-22P. The rat and human DRR receptors can be used to screen compounds which either mimic the action of BAM-22P (agonists) or antagonize the action of BAM-22P (antagonists).

Screening assays can be performed using the FLIPR assay described above. Alternatively, BAM-22P can be iodinated and used as a tracer in radioligand binding assays on whole cells or membranes. Other assays that can be used include the GTPãS assay, adenylyl cyclase assays, assays measuring inositol phosphates, and reporter gene assays (e.g., those utilizing luciferase, aqueorin, alkaline phosphatase, etc.).

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

The invention claimed is:

1. A method of assaying a test compound for its ability to bind to a human dorsal root receptor (DRR), comprising:
   a) incubating a cell expressing a human DRR or membranes prepared from said cell with bovine adrenal medulla docosapeptide (BAM-22P) (SEQ ID NO: 1) in the presence or absence of a test compound; and
   b) detecting displacement of the binding of said BAM-22P to said DRR wherein displacement of said binding is indicative of a compound that binds a human DRR.

2. The method of claim 1, wherein said cell expressing DRR is a recombinant cell expressing a heterologous DRR.

3. The method of claim 1, wherein said assay is a radioligand assay and said BAM-22P or said test compound is radioactively labeled.

4. The method of claim 1, wherein said assay is an enzyme-linked immunosorbent assay (ELISA) and either said BAM-22P or said test compound is joined to an enzyme.

* * * * *

SEQUENCE LISTING

<160> NUMBER OF SEQ ID NOS: 1

<210> SEQ ID NO 1
<211> LENGTH: 22
<212> TYPE: PRT
<213> ORGANISM: Homo sapiens

<400> SEQUENCE: 1

Tyr Gly Gly Phe Met Arg Arg Val Gly Arg Pro Glu Trp Trp Met Asp
1               5                   10                  15

Tyr Gln Lys Arg Tyr Gly
            20